United States Patent [19]

Serpelloni et al.

[11] Patent Number: 5,679,398
[45] Date of Patent: Oct. 21, 1997

[54] PARTIALLY MELT CO-CRYSTALLIZED XYLITOL/SORBITOL AND A PROCESS FOR OBTAINING THE SAME

[75] Inventors: Michel Serpelloni, Beuvry les Bethune; Alain Croisier, Locon, both of France

[73] Assignee: Roquette Freres, Lestrem, France

[21] Appl. No.: 385,786

[22] Filed: Feb. 9, 1995

Related U.S. Application Data

[63] Continuation of Ser. No. 141,090, Oct. 26, 1993, abandoned, which is a continuation of Ser. No. 807,128, Dec. 16, 1991, Pat. No. 5,385,749.

[30] Foreign Application Priority Data

Dec. 14, 1990 [FR] France .................. 90 15708

[51] Int. Cl.⁶ .................................................. A23G 3/00
[52] U.S. Cl. .................................... 426/658; 426/660
[58] Field of Search .................................. 426/658, 660

[56] References Cited

U.S. PATENT DOCUMENTS

| | | | |
|---|---|---|---|
| 3,195,868 | 7/1965 | Loomans et al. | 259/104 |
| 3,899,593 | 8/1975 | Hammond et al. | 426/3 |
| 4,284,650 | 8/1981 | Goupil | 426/5 |
| 4,831,129 | 5/1989 | Serpelloni | 536/124 |
| 5,023,092 | 6/1991 | DuRoss | 426/3 |
| 5,045,340 | 9/1991 | Kohler | 426/660 |
| 5,158,789 | 10/1992 | DuRoss | 426/3 |

FOREIGN PATENT DOCUMENTS

| | | |
|---|---|---|
| 0 305 356 | 3/1989 | European Pat. Off. . |
| 0 329 977 | 8/1989 | European Pat. Off. . |
| B-49-016929 | 4/1974 | Japan . |
| 1 526 020 | 9/1978 | United Kingdom . |

OTHER PUBLICATIONS

Derwent File supplier WPI, 1974, AN=74-39213V [21], Derwent Publications Ltd, Londres, GB; & JP-B-49 016 929 (Towa Kasei Kogyo K.K.) Abstract.
Ltd, Londres, GB; & JP-B-49 016 929 (Towa Kasei Kogyo K.K.) Abstract.
Acta Pharmaceutica Fennica 87,61-73 (1978).
Acta Pharmaceutica Fennica 91,47-54 (1982).

*Primary Examiner*—Raymond Henley, III
*Attorney, Agent, or Firm*—Larson & Taylor

[57] ABSTRACT

The present invention relates to a directly compressible pulverulent composition based on xylitol, characterized in that it has a compressibility, determined in a test A, above 70N. The invention also relates to the process of fabrication of the said directly compressible pulverulent composition and the use of the said composition for the fabrication of tablets or articles of confectionery, in particular of the chewing gum type.

14 Claims, 2 Drawing Sheets

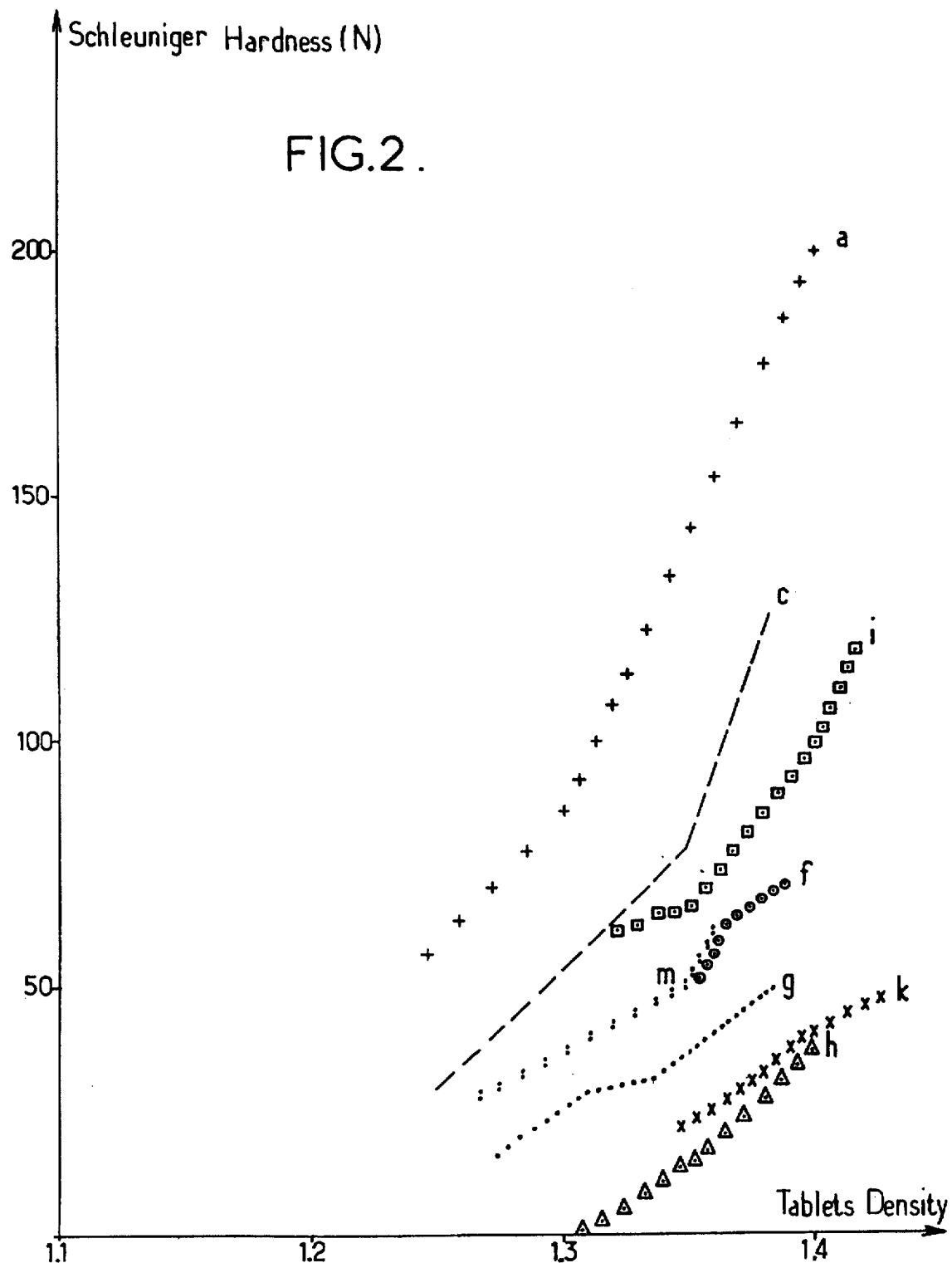

PARTIALLY MELT CO-CRYSTALLIZED XYLITOL/SORBITOL AND A PROCESS FOR OBTAINING THE SAME

This is a continuation of application Ser. No. 08/141,090, filed Oct. 26, 1993, now abandoned, which is a continuation of application Ser. No. 07/807,128, filed Dec. 16, 1991, now U.S. Pat. No. 5,385,749.

The present invention relates, by way of novel industrial product, to a directly compressible pulverulent composition based on xylitol.

It also has as its object a process for the preparation of this pulverulent composition.

Further, it relates to the use of this pulverulent composition as sweetening filled in tablets and articles of confectionery of the chewing gum type.

More specifically, the present invention concerns a partially melt co-crystallized xylitol/sorbitol and a process for its preparation.

Xylitol, which is a pentavalent alcohol sugar is a sweet crystalline product, white in colour, odourless and soluble in water. In crystalline form, it has a negative dissolving heat and thereby produces an agreeable refreshing or cooling effect in the mouth. This property is particularly advantageous in pharmaceutical or food tablets.

In addition to its cooling effect, xylitol has interesting sweetening qualities. If one takes sucrose as reference point and attributes to it a sweetening value of 1, xylitol is found to have a sweetening value of the same order whereas for more traditional polyols such as sorbitol or mannitol the values are, respectively, 0.60 and 0.45.

Like other alcohol sugars already used in the food industry and pharmacy, xylitol is an advantageous sucrose substitute for diabetics.

Moreover, xylitol has an interesting property for dental health, in which it differs from other known polyols. It is in fact not only acariogenic, that is to say it can not serve as substrate for bacteria present in the mouth cavity, but it also plays a role in preventing dental caries.

It is thus on several grounds that the use of xylitol would be justified as binder and diluent in the fabrication of tablets.

It is well known that certain powders are by their nature difficult to compress. This is unfortunately the case with crystallised pulverulent xylitol, which therefore cannot be obtained as sufficiently hard tablets. Its limit of compressibility is relatively low, so that it favours the appearance of the phenomenon of capping, that is to say splitting of the tablet in a diametric plane which eliminates all its cohesion. Such a tablet is very friable and has the tendency to break into two or more parts when tested for hardness or even when ejected from the press.

One of the known techniques for conferring the capacity for compression on powders is moist granulation. This is a expensive and relatively complicated process to carry out in which supplementary additives are used as binders, such as starch, cellulose or gelatine. As regards xylitol, it is well known that this product is very difficult to granulate under moist aqueous conditions due to its hygroscopic character and its very high solubility in water. It is therefore necessary to use non-aqueous solvents such as polyethylene glycol or ethanol, which, however, do not have the same advantages as water from the aspect of economics and toxicity. Moreover, the compressibility of xylitol granules prepared by this method is not good, see Acta Pharmaceutica, Fennica 87, pages 61 to 73 (1978) and 91, page 48 (1982).

The technique of so called direct compression without previous treatment of the powder thus remains the most advantageous method for the pharmaceutical industry and food industry, in particular from an economical point of view.

In attempting to render xylitol directly compressible, it was initially proposed to mix crystallised pulverulent xylitol with different known binders such as microcrystalline cellulose, see Acta Phrmaceutica, Fennica 91, pages 47–54 (1982). Apart from the fact that this compound is insoluble, so that it would be difficult to use for tablets which are to be sucked, which are the most common form of tablets used in the food industry, it should be noted that microcrystalline cellulose is present in a proportion of 10 to 50% by weight, based on the xylitol. It therefore has the tendency to mask the expression of certain advantageous properties of crystalline xylitol such as its sweetening power, its cooling effect and its agreeable taste. This obviously reduces the interest in using compressed crystallised xylitol. Moreover, the economical incidence of incorporating microcrystalline cellulose is not to be neglected as this is a relatively expensive additive. Lastly, the presence of binder is not greatly favoured by the manufacturers of compressed products, in particular for pharmaceutical purposes.

It has also been proposed in French Patent Application No.2 336 123 to produce tablets which are to be chewed from a dry mixture of xylitol in a quantity of 10 to 80% by weight and a polyol in a quantity of 10 to 80% by weight, based on the weight of the tablet. The polyol may be sorbitol, mannitol or a mixture of these two. It appears from the description of the said Patent Application that the polyol amounts to at least 50% by weight of the xylitol. The latter therefore cannot be regarded as the main constituent of the powder to be compressed. Under these conditions, it is not possible to obtain optimum benefit from all the advantages of xylitol.

European Patent Application No. 305 356 describes a process for the preparation of granulated products suitable for direct compression. In this process, a pulverulent product, which may be xylitol, is brought into contact under conditions of stirring with a liquid consisting of the same product in the molten state, and the mixture obtained is then rapidly cooled.

Due to this last arrangement, the product obtained is present to a non-negligible proportion in an amorphous form. This may entail certain disadvantages, in particular a loss of cooling effect, a greater hygroscopicity and hence a tendency of the powder to clump together, and low compressibility. It will also be noted that this process is relatively delicate to carry out. Moreover, it has been verified that the granular product obtained has poor characteristics of friability and cannot be used for preparing tablets having properties of compression, in particular hardness, compared with tablets obtained with conventional crystallised xylitol.

In a process for agglomerating very fine crystallised xylitol powder by means of a sorbitol syrup under vigorous stirring, the owner of European Patent Application No. 329 977 proposes a binding agent and diluent which can be used for direct compression, the granules having a particle size of about 0.1 to 1 mm and containing 95 to 98% by weight of xylitol, 1 to 5% by weight of sorbitol, 0 to 2% by weight of other polyols and less than 1% by weight of water. This agent has an apparent density ("bulk density") of from 0.7 to 0.8 g/cm$^3$.

Previous crushing of xylitol for obtaining a fine particle size, agglomeration with a sorbitol syrup having a low solids content and final drying of the powder do not amount to a process having the desired simplicity and they constitute additional operations which increase the operating costs.

Besides, it has been found that the results obtained in terms of hardness of the tablets prepared with this binding agent and diluent are not satisfactory.

It is on the basis of these last findings and in view of all the disadvantages of the other processes known in the art that the Applicant has sought to provide a pulverulent composition for direct compression based on xylitol, that is to say a composition mainly consisting of this polyol, and having improved properties of compressibility and flow compared with existing pulverulent products containing xylitol.

As a result of numerous studies and tests, the Applicant has succeeded in preparing a directly compressible pulverulent composition based on xylitol, characterised by a compressibility, determined by a test A, above 70N and preferably above 80N.

In particular, the Applicants have succeeded in preparing a partially melt co-crystallized xylitol/sorbitol having a compressibility determined by Test A, above 70N.

This value for compressibility is surprisingly and unexpectedly greatly superior to the values obtained with xylitol-based compositions hitherto known until now.

The proportion of xylitol in the composition is preferably greater than or equal to 60% by weight and more preferably 80% by weight.

Test A consists of measuring the force, expressed in Newtons, representing the compressibility of the composition under investigation which is necessary for crushing a tablet prepared from the said composition, that is to say for producing the appearance of fracture lines inside the mass of the tablet, this force thus corresponding to the resistance to crushing of the tablet which is cylindrical in form with flat surfaces having a diameter of 13 mm and with a thickness of 4 mm and a weight of 0.717 g, that is to say an apparent volumetric mass or density of 1.35 g/ml, the said force being exerted against the peripheral surface of the tablet in the direction of the axis of revolution of the tablet by means of a movable stop applying a thrust against the said surface along a generatrix. During this test, the tablet is held against a fixed stop also applied against the peripheral surface of the tablet along a generatrix which is diametrically opposite to that against which the movable stop is applied.

These tablets are prepared by adding 2% by weight of lubricant, namely magnesium stearate, to the composition under investigation.

These two products are homogenised with one another by means of a TURBULA T2C mixer (marketed by WILLY A. BACHOFEN AG, Switzerland) for five minutes at a driving speed of 42 revolutions/minute.

To compress the obtained mixture, a FROGERAIS reciprocating press of type AM is used. This press is equipped with round punches with plane surfaces having a diameter of 13 millimetres.

To obtain the characteristics of the tablets mentioned above, the press is adjusted to regulate the amount by which the upper punches press in and the filling volume of the matrix, the latter arrangement being used to fix the desired quantity by weight of the pulverulent mixture, which in the present case is 0.717 g.

The resistance of these tablets to crushing is determined by means of a SCHLEUNIGER 2E durometer (marketed in France by FROGERAIS Establisments).

The composition according to the invention contains at least one additive selected from saccharides, oligosaccharides and polysaccharides and their corresponding hydrogenated compounds, that is to say organic molecules characterised by the presence of carbon chains carrying hydroxyl groups and aldehyde, ketone or acid functions.

The additives chosen are preferably sugars such as aldoses or ketoses and their hydrogenated derivatives, for example sorbitol, mannitol or maltitol and polysaccharides, in particular polymers of glucose such as maltodextrins having a Dextrose Equivalent below 20, or glucose syrups, and their hydrogenated derivatives.

According to one advantageous arrangement of the invention, the additive is selected from the following list of compounds, which is not limiting: Sorbitol, maltitol, mannitol, maltodextrin. In a preferred embodiment for carrying out the invention, the additive selected is sorbitol.

It goes without saying that the invention is not limited to the use of only one additive in addition to xylitol but also covers any composition containing several additives differing in nature.

The present invention also relates to a process for the preparation of the said pulverulent composition based on xylitol.

According to this process, a starting material substantially consisting of xylitol, that is to say containing a quantity of xylitol greater than or equal to 60%, preferably 80%, and at least one additive, is subjected to extrusion treatment inside an extrusion apparatus containing a heat treatment zone and at least one extrusion die, the rate of supply of xylitol and additive to the apparatus and the parameters for the extrusion treatment, namely the temperature inside the heat treatment zone, the diameter of the extrusion die and the speed of transport of the starting material inside the heat treatment zone, being selected so that the mixture of xylitol and additive will be partially melted at the outlet of the die and before it leaves the die.

The pulverulent composition based on xylitol according to the invention is also defined as being a pulverulent composition obtainable by the process according to the invention.

The above said installation is preferably of the double screw type having at least one extrusion die and the parameters for the extrusion treament are selected so that the starting material is at a temperature of from 75 to 110° C. inside the die and before its discharge from the die, the said temperature depending on the nature and quantity of the additive or additives put into the process.

This temperature may easily be determined by the man of the art as he knows that the melting temperature of xylitol is in the region of 92° C. and the proportion of molten starting material is preferably from 30 to 90%, more preferably from 50 to 80%, so that the product obtained at the extrusion outlet has a viscosity which enables it to be easily and rapidly subjected to the subsequent operations of the process.

If the pulverulent composition contains a single additive and the latter is, sorbitol, the temperature of the starting material inside the die and before the outlet of the die is preferably from 80° to 105° C.

If the single additive is maltitol, the said temperature is preferably from 80° to 100° C.

Advantageously, the xylitol and additive which constitute the starting material to be extruded are in a pulverulent form and may or may not be crystallised.

The invention further relates to other arrangements preferably used at the same time which will be more particularly described below, and it will be better understood with the aid of the description given below with the attached FIGS. 1 and 2 and examples.

BRIEF DESCRIPTION OF THE DRAWINGS

FIG. 2 is a graph comparing the compressibility of the composition of the invention with compositions of the prior art.

Figure 1:
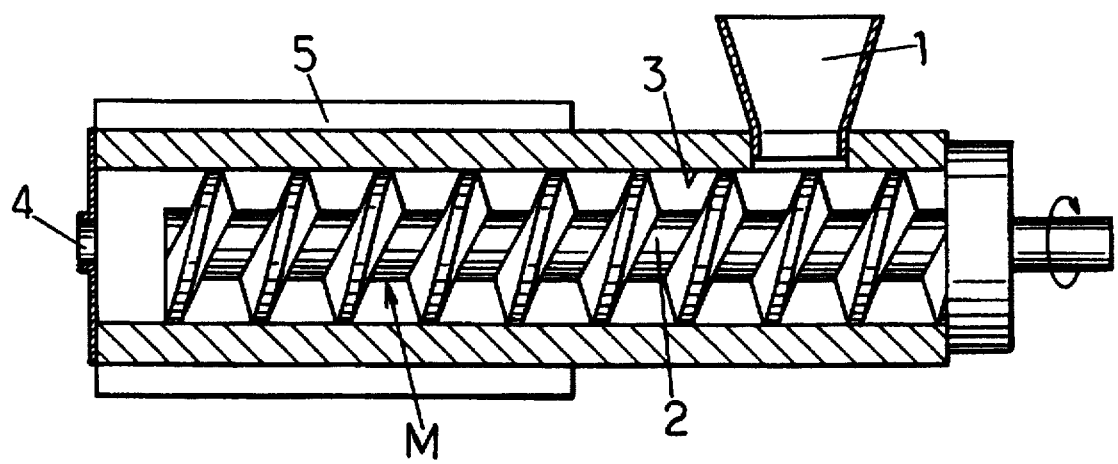
FIG. 1 is schematic section through an extrusion apparatus suitable for use in the process according to the invention.

The following method or an equivalent method is employed for fabricating a directly compressible pulverulent composition based on xylitol according to the invention:

The starting material which is subjected to the extrusion treatment by the process according to the invention consists, for example, of a mixture of 90% by weight of xylitol powder and 10% by weight of sorbitol powder.

In practice, crystallised xylitol and sorbitol obtained by the techniques conventionally employed in this field are used.

The extrusion apparatus advantageously consists double screw-type extruder comprising, as shown in FIG. 1:

a feed device, in particular a feed hopper 1, a mixing device M comprising an endless double screw system 2 inside a housing 3 in particular of nitrided steel rotated by a not shown mechanism, an outlet comprising one or more extrusion dies 4 of differing forms, means for thermal regulation 5 to control the temperature of the mixing zone, the said means 5 consisting on the one hand of heating means, for example, formed by electric resistors or by a heating system operating by induction or steam, and on the other hand of not shown cooling means arranged outside the housing or on the inside and consisting, for example, of cooling coils located in the housing, and/or of a circulation of cooling fluid inside the screw.

The starting material introduced into the mixing zone from the feed system is subjected to shearing forces and intense mechanical friction by the compression in the turns of the screw and at the same time to heating induced by the heating means employed.

The extrusion consequently consists of a thermomechanical treatment.

It should be noted that good results have been obtained with a double screw-type extruder marketed under the name of "BC 82" by CLEXTRAL Company. The two screws intermesh and turn in the same sense. The mixing zone is heated by induction or cooled by circulation of a cooling fluid in a coil so that the temperature can easily be regulated.

The main advantage of this heating method is the flexibility in use and the ease of control by means of a simple control loop (thermocouple/control device of the heating means by induction of the cooling means).

The installation used in this example comprises four cylindrical extrusion dies 5 mm in diameter.

The temperature of the heat treatment zone is obtained by imposing a predetermined value on the control system. In the case of the extrusion apparatus in question, this value is from 75° to 110° C., preferably from 80° to 105° C.

The mechanical characteristics of the screws and their speed of rotation are chosen so that the residence time of the starting material inside the heat treatment zone will be from 5 to 300 s.

As a result of the choice of all these parameters, the temperature of the starting material which has been subjected to the treatment is from 75° to 110° C. inside the dies and before exit from the latter.

The coextruded mixture based on xylitol obtained at the outlet from the extrusion apparatus is then subjected successively to:

cooling, crushing and sifting.

According to another feature of the present invention, the pulverulent composition according to the invention is found to be particularly suitable as sweetener for confectionery and in particular confectionery of the chewing gum type.

One of the classical problems confronting manufacturers in the industrial production of chewing gums is the lack of "machinability" of the mass of basic gum and the processed sweetening filler. This mass is conventionally handled at a temperature of 40°–50° C. It is important that the mass should be sufficiently soft at this temperature to enable all the components of the chewing gum (basic gum, sweetening filter, flavouring substances, coloring substances . . . ) to be mixed homogeneously but not too soft in order to avoid problems of sticking during the stages of mixing, forming and cutting.

The sweetening filler has a significant influence on the viscosity of the processed work mass. It is known, for example, that if the sweetening filler is a powder, good hardness at a high temperature can be obtained if the granulometry is very fine. The disadvantage of these fine powders is their very high hygroscopicity, with the result that they tend to clump together during storage.

It is surprisingly and unexpectedly found that the composition according to the invention enables chewing gums to be obtained which have very good hardness both in the hot and cold state without requiring very fine granulometries. Moreover, the organoleptic quality of these chewing gums is entirely satisfactory.

The present invention thus also relates to the use of the pulverulent composition based on xylitol according to the invention as sweetening filler in confectionery of the chewing gum type as well as relating to the confectionery products thus obtained.

The very sweet flavour, the cooling effect and the cariostatic effect of xylitol are properties which are particularly appreciated for the use of this product in confectionery of the chewing gum type.

The examples given below illustrate the significant differences between the pulverulent compositions according to the invention and products based on xylitol for direct compression either produced according to the prior art or produced for comparison purposes by the Applicant Company, and the advantages obtained by the use of the said pulverulent compositions in confectionery of the chewing gum type.

EXAMPLES RELATING TO THE USE UNDER COMPRESSION

The following are used in these examples:

Five different samples of the pulverulent composition according to the invention, indicated by the references a, b, c, d and e;

a sample of XYLITOL DC marketed by CULTOR Company and indicated by the reference f;

a sample of extruded xylitol powder having a minimum chemical purity of 99% by weight of dry substance and indicated by the reference g;

a sample of pulverulent xylitol marketed by ROQUETTE Company and having a minimum chemical purity of 99% by weight of dry substance, indicated by the reference h;

three samples of pulverulent mixtures containing xylitol powder and sorbitol powder marketed by ROQUETTE Company, having a chemical purity of, respectively, 99% and 96% by weight of dry substance, in which the xylitol powder and sorbitol powder are mixed together in the dry state; the proportions by weight of these xylitol/sorbitol mixtures are, respectively, 50/50 for the sample indicated by the reference i, 90/10 for the sample indicated by the reference k and 95/5 for the sample indicated by the reference l;

a sample j of compressible xylitol prepared by the process described in Patent Application EP 0 305 356 by mixing 300 g of molten xylitol at a temperature of about 100° C. and 700 g of crystallised xylitol;

and two samples of pulverulent mixtures consisting of xylitol and sorbitol which have been extruded separately and then mixed together in the dry state; the minimum chemical purities of the xylitol and sorbitol are, respectively, 99% and 96% by weight of dry substance; the proportions by weight of these xylitol/sorbitol mixtures are, respectively, 90/10 for the sample indicated by the reference m and 98/2 for the sample indicated by the reference n.

The five samples f to j belong to the prior art and the four samples k to n were selected and prepared by the Applicant for comparison purposes.

1. Preparation of five samples a–e according to the invention

For the three samples a–c, the additive chosen is sorbitol of the type marketed by the Applicant under the trade mark NEOSORB® P60. The quantities of sorbitol are, respectively, 10%, 5% and 2% by weight based on the composition for samples a, b and c. For sample d, the additive chosen is pulverulent maltitol present in a proportion of 10% by weight, based on the composition.

Lastly, for sample e, the additive chosen, which is present in a proportion of 10% by weight, based on the composition, consists of a maltodextrin obtained by enzymatic hydrolysis of starch and having a Dextrose Equivalent or D.E. (number of grams of reducing sugars expressed as dextrose to 100 grams of dry product) of 12, marketed by the Applicant under the Registered Trade Mark GLUCIDEX® 12.

The xylitol used in each of the samples a to e is obtained by crystallisation in water and contains a minimum of 99% of xylitol by weight, based on the solids content.

Samples a to e are prepared by introducing a homogeneous pulverulent mixture of xylitol and additive into the extruder in the proportions indicated above. The extruder used is of the type mentioned above, that is to say "BC 82" of CLEXTRAL Company.

The speed of the screws is controlled so that the output of the installation is 200 kg/hour and the time taken for the starting material to pass through the apparatus is about 30 s.

The predetermined temperature of the heating system is programmed to a value from 85° to 110° C., varying according to the nature and quantity of the additive.

For samples a to e, the temperatures chosen are as follows:

sample a≈90° C.,
sample b≈92° C.,
sample c≈93° C.,
sample d≈90° C.,
sample e≈92° C.

At the exit from the extruder and after cooling, the coextruded mixtures of xylitol/additives are in the form of small sticks which are crushed in a hammer mill.

The fraction held back has a particle size above 50 microns, more generally above 100 microns.

2. Tests

For each of the samples a to n tested, an average particle size of from 400 to 900 microns was selected.

Using the CARR method as described by R. L. Carr in Chem. Eng. 72, No.163, 168 (1985) and Chem. Eng. 72, No.2, 69–73 (1985), the flow index and the density of powders a to n are measured. The apparatus used for this test is the one known under the trade mark HOSOKAWA POWDER TESTER manufactured by MICROMERITICS, Osaka (Japan).

In addition, the friability of some of the pulverulent compositions a to m are determined. This property is characterised by the percentage of particles which have not resisted crushing in a friability measuring apparatus. In the present case, the apparatus of Trade Mark ERWEKA TA was used. This apparatus contains five identical steel balls 1.7 cm in diameter, each weighing 18.87 g. 15 g of a fraction measuring 400 to 500 microns of the tested powder are introduced and the apparatus is rotated at the rate of 25 revolutions per minute for 15 minutes. At the end of the crushing operation, the proportion held back by a sifter having a mesh of 351 microns, expressed as a percentage, is determined by weighing. The friability then corresponds to the amount required to make this value up to 100 g. The larger the number so obtained, the greater is the friability.

The compressibility of these samples is then determined by test A defined above.

The results of these measurements of compressibility by test A and the mean granulometry, the flow indices and the friability of the tested samples are summarized in the Table below.

| Pulverulent compositions based on xylitol | Samples a to e according to the invention | | | | | Samples f to j of the prior art | | | | | Comparison samples k to n | | | |
|---|---|---|---|---|---|---|---|---|---|---|---|---|---|---|
| | a | b | c | d | e | f | g | h | i | j | k | l | m | n |
| Xylitol content | 90 | 95 | 98 | 90 | 90 | 98 | 100 | 100 | 50 | 100 | 90 | 95 | 90 | 98 |
| Mean granulometry in microns | 700 | 750 | 810 | 820 | 840 | 410 | 675 | 700 | 650 | 480 | 680 | 690 | 700 | 810 |
| Powder density | 0.720 | 0.760 | 0.809 | 0.771 | 0.746 | | | | | 0.730 | | | | |
| Water content (%) | 0.40 | 0.30 | 0.25 | 0.30 | 0.60 | 0.30 | | | | | | | 0.30 | |
| Flow (CARR) | | | | ABOVE | | | | 75 | | | | | | |
| Friability (%) | 63 | 71 | 82 | 78 | 80 | 93 | | | | | | | 80 | |
| Compressibility (Resistance to breakage) in M for d = 1.35 | 144 | 130 | 83 | 89 | 102 | 49 | 40 | 15 | 65 | 65 | 25 | 25 | 53 | 48 |

This Table shows that the pulverulent composition according to the invention has a substantially increased compressibility or resistance to crushing which is always greater than 70N. By comparison, sample f consisting of XYLITOL DC of CULTOR Company and conforming to the sample described and claimed in European Patent Application No. 0 329 977 has a compressibility of only 49N, that is to say three times less than that of the sample according to the invention (144N). The same applies to sample j corresponding to the xylitol described in European Patent Application No. 0 305 536.

These extremely significant differences clearly show the surprising and unexpected character of the performances under compression of the pulverulent composition according to the invention.

It should also be noted that the compressibility of a composition obtained from a dry mixture of 50/50 of xylitol and sorbitol (sample i), that is to say corresponding to the characteristics claimed in French Patent Application No. 2 336 123 mentioned above, only reaches a value of 65N, which is thus substantially below 83N, not to mention 144N of the compositions according to the invention. This disadvantage is added to the fact that 50% of sorbitol is a very high proportion of sorbitol and correspondingly diminishes the proportion of xylitol present and prevents full benifit being obtained from the advantageous properties of xylitol when consumed.

The table also shows that the pulverulent composition according to the invention advantageously has improved friability characteristics compared with those of powders of the prior art and the comparison powders.

To illustrate more graphically the improvement in the performances under direct compression of the compositions according to the invention compared with that of compositions of the prior art, the attached FIG. 2 contains for each of the samples a, c, f, g, h, i, k and m a graph giving the variation in compressibility in N as a function of the density or apparent volumetric mass of tablets in g/ml.

Tablets of differing densities are manufactured by the same method as that described above, using an AM. FROG-ERAIS reciprocating press. Different densities of tablets are obtained by varying the quantity by weight of powder used for preparing a tablet. The greater this quantity, the higher is the density of the tablet and the greater is the force of compression required for obtaining a tablet of the given dimensions.

It is found on the basis of FIG. 2 that the compressibility of compositions a and c of the invention is always substantially above that of compositions f, g, h, i and j of the prior art and of comparison compositions k, m, no matter what the density of the tablets.

This FIG. 2 also shows that samples a and c of the invention having proportions of xylitol/sorbitol of 90/10 and 98/2, respectively, are more readily compressed than extruded crystallised xylitol (sample g) and xylitol crystallised in water (sample h).

If one compares the characteristic graphs of samples a and f, that is to say those corresponding to, respectively, the coextruded 90/10 xylitol/sorbitol composition according to the invention and the 98/2 xylitol/sorbitol composition of XYLITOL DC of CULTOR Company (sorbitol added in the form of an aqueous syrup to the xylitol powder) according to Patent Application EP 329 977, the compression of the composition according to the invention is found to be substantially superior no matter what the density of the tablet.

There was nothing to predict such an improvement in performances, bearing in mind that sorbitol was used in combination with xylitol in both cases.

As regards the non-extruded mixtures of xylitol/sorbitol in the proportions of 50/50 (sample i) according to Patent Application FR 2 336 123 and 90/10 (comparison sample k), the difference between curve a and curves i and k again demonstrates the very advantageous character of the compositions according to the invention. Even for sample k, which is equivalent in the proportions by weight of xylitol/sorbitol to the sample according to the invention, the superiority of compression of the latter is clear from an inspection of curves a and k.

Curve m obtained with comparison sample m containing 90% of xylitol and 10% of sorbitol extruded separately shows the lower compressibility of this sample compared with samples a to c of the invention. The compressibility cannot be improved by simply mixing xylitol and sorbitol which have been extruded separately. Consequently, even if this solution had been described in the prior art, it would certainly not have given any suggestion to the man of the art to resort to extrusion and still less to co-extrusion in order to confer a satisfactory compressibility on xylitol. All the more therefore is it to the merit of the Applicant to have taken this step to arrive at the invention.

EXAMPLE RELATING TO THE USE IN CONFECTIONERY OF THE CHEWING GUM TYPE

This Example has been provided to compare the hardness and organoleptic qualities of sugar-free chewing gums prepared on the one hand with sample g of known pulverulent xylitol (crystallised in water) and on the other hand with the pulverulent composition according to the invention.

The granulometries of the two powders a and g are identical. They contained no particles greater than 160 microns.

| Composition of chewing gums | |
|---|---|
| Basic gum (basic gum 34/42 of DREYFUS Company) | 33% by weight |
| Sweetening filler | 65% by weight |
| Lecithin (Mc Thin AF1 of LUCAS MEYER Company) | 0.5% by weight |
| Mint flavour | 1.5% by weight |

Method

Preheat the basic gum to 40°–50° C. and introduce into a kneading machine. Knead for 2 minutes Add half the quantity of pulverulent sweetening filler and the flavouring substance and knead for 3 minutes Add the lecithin and knead for 1 minute Add the reminder of the sweetening filler then knead for 4 minutes.

Results

The hardnesses of chewing gums at different temperatures after a given storage time following their manufacture and after different storage times at a temperature of 20° C. was measured by penetrometry, using an INSTRON-type apparatus.

The results are shown in the Table below.

| Conditions of measurement | Chewing gum prepared with Sample g | Chewing gum prepared with Sample a according to the invention |
|---|---|---|
| 45° C. | 1.82 | 3.00 |
| 35° C. | 6.57 | 8.82 |
| 24° C. | 20.54 | 24.96 |

| Conditions of measurement | Chewing gum prepared with Sample g | Chewing gum prepared with Sample a according to the invention |
|---|---|---|
| after 1 day at 20° C. | 23.65 | 26.60 |
| after 15 days at 20° C. | 25.67 | 30.05 |

This table clearly shows that the composition a according to the invention confers greater hardness in the heat to chewing gum than that obtained with sample g of the prior art.

The chewing gums containing Sample a according to the invention can thus be manufactured more easily. The machinability of the mass being processed is substantially improved and the problems of sticking to the equipment are easily prevented.

As concerns the hardness in the "cold" (20° C.), the chewing gums containing Sample a also have greater hardness than the chewing gums prepared with sample g but the hardness remains within acceptable limits.

It is also found that the hardness of these two types of chewing gums varies substantially in the same manner in the course of storage at this temperature of 20° C.

Concerning the appearance and structure of the chewing gums obtained, it is found that chewing gums prepared with Sample a have the advantage of a more homogeneous and bonded structure and of being whiter than those prepared with Sample g of the prior art.

Lastly, concerning the organoleptic properties, the chewing gums of type a and those of type g are comparable but the sweetening effect is more prolonged in type a chewing gum.

The advantages of using the pulverulent composition according to the invention will be clearly seen from the example given above.

It is to be understood and will be obvious from what has been said above that the invention is in no way limited to those modes of application and embodiment which have been more particularly considered but indeed covers all the variations.

We claim:

1. Partially melt co-crystallized xylitol/sorbitol having a compressibility determined by Test A, above 70N.

2. Partially melt co-crystallized xylitol/sorbitol in accordance with claim 1, having a compressibility determined by Test A, above 80N.

3. Partially melt co-crystallized xylitol/sorbitol in accordance with claim 1, wherein the quantity of xylitol is greater than or equal to 60 percent by weight.

4. Partially melt co-crystallized xylitol/sorbitol in accordance with claim 1, wherein the quantity of xylitol is greater than or equal to 80 percent by weight.

5. Partially melt co-crystallized xylitol/sorbitol in accordance with claim 1, consisting of 90 percent by weight xylitol and 10 percent by weight sorbitol.

6. Partially melt co-crystallized xylitol/sorbitol in accordance with claim 1, consisting of 95 percent by weight xylitol and 5 percent by weight sorbitol.

7. Partially melt co-crystallized xylitol/sorbitol in accordance with claim 1, consisting of 98 percent by weight xylitol and 2 percent by weight sorbitol.

8. An ingestible composition comprising partially melt co-crystallized xylitol/sorbitol having a compressibility determined by Test A, above 70N.

9. An ingestible composition in accordance with claim 8, wherein the composition is in the form of a tablet.

10. A process for the preparation of partially melt co-crystallized sorbitol/xylitol having a compressibility determined by Test A, above 70N, comprising the step of subjecting a starting material comprising xylitol and sorbitol to an extrusion treatment inside an extrusion apparatus comprising a heat treatment zone and at least one extrusion die, the rate of supply of starting material to the apparatus as well as the parameters for the extrusion treatment, namely the temperature existing inside the treatment zone, the diameter of the extrusion die and the speed of transport of the starting material inside the heat treatment zone, being selected so that the starting material will be partially melted at the outlet of the die and before it leaves the die.

11. A process according to claim 10, wherein the extrusion apparatus is of the double-screw type comprising at least one extrusion die, the parameters of the extrusion treatment being selected so that the starting material is at a temperature of 75°–110° C. inside the die and before the outlet of the die.

12. A process according to claim 10, wherein the starting material is in a pulverulent form.

13. A process according to claim 10, wherein the proportion of molten starting material is from 30–90 percent by weight.

14. A process according to claim 10, wherein the proportion of molten starting material is from 50–80 percent by weight.

* * * * *